(12) United States Patent
Fish

(10) Patent No.: US 7,004,901 B2
(45) Date of Patent: Feb. 28, 2006

(54) METHOD AND KIT FOR THE TRANSDERMAL DETERMINATION OF ANALYTE CONCENTRATION IN BLOOD

(76) Inventor: Falk Fish, 4 Hakim St. 69120, Tel Aviv (IL)

( * ) Notice: Subject to any disclaimer, the term of this patent is extended or adjusted under 35 U.S.C. 154(b) by 64 days.

(21) Appl. No.: 10/381,704

(22) PCT Filed: Sep. 6, 2001

(86) PCT No.: PCT/IL01/00848

§ 371 (c)(1),
(2), (4) Date: Jul. 25, 2003

(87) PCT Pub. No.: WO02/27326

PCT Pub. Date: Apr. 4, 2002

(65) Prior Publication Data

US 2004/0030228 A1    Feb. 12, 2004

(30) Foreign Application Priority Data

Sep. 29, 2000 (IL) .................................... 138788

(51) Int. Cl.
*A61B 5/00* (2006.01)
*G01N 33/66* (2006.01)
(52) U.S. Cl. .................. 600/309; 436/95; 600/365
(58) Field of Classification Search ........ 600/309–310, 600/300, 316, 322; 436/93–95; 435/14; 422/68.1
See application file for complete search history.

(56) References Cited

U.S. PATENT DOCUMENTS

| | | | |
|---|---|---|---|
| 4,151,270 A * | 4/1979 | Ream et al. .................. | 424/48 |
| 5,362,307 A | 11/1994 | Guy et al. | |
| 5,817,012 A * | 10/1998 | Schoendorfer .............. | 600/362 |
| 6,021,339 A * | 2/2000 | Saito et al. ................. | 600/345 |
| 6,070,093 A * | 5/2000 | Oosta et al. ................ | 600/316 |
| 6,102,872 A * | 8/2000 | Doneen et al. ............. | 600/582 |
| 6,272,364 B1 * | 8/2001 | Kurnik ....................... | 600/345 |

FOREIGN PATENT DOCUMENTS

| | | |
|---|---|---|
| WO | WO 97/02811 | 1/1997 |
| WO | WO 99/13336 | 3/1999 |
| WO | WO 99/22639 | 5/1999 |
| WO | WO 99/67645 | 12/1999 |
| WO | WO 00/11469 | 3/2000 |

OTHER PUBLICATIONS

Ben-Ayreh, Hanna, et al., "Salivary Composition in Diabetic Patients". J. Diabet. Complications, vol. 2, pp. 96-99, 1988.
Forbat, L. N., et al., "Glucose concentrations in partoid fluid and venous blood of patients attending a diabetic clinic". J. R. Soc. Med., vol. 74, pp. 725-728, Oct., 1981.
Hertig, B. A., et al., "Time course of sweating in warm baths". Included on Montagna, W., et al. (eds.), Advances in Biology of Skin, vol. III Eccrine Sweat Glands and Eccrine Sweating, pp. 213-225, Pergamon Press, Oxford, 1962.
Kuno, Yas, "Human Perspiration". Chapter V, "Perspiration of the Palms and Soles and the Effect of Mental Stress on Perspiration in General". Charles C. Thomas, Publisher, Springfield, Illinois, 1956.
Patrick, A. W., et al., "Home Glucose Monitoring in Type 2 Diabetes: Is It a Waste of time?". Diabet. Med., vol. 11, pp. 62-65, 1994.
Rothman, Stephen, "Physiology and Biochemistry of the Skin". Chapter 19, "Carbohydrates". The University of Chicago Press, 1954.
Sönksen, P. H., "Home monitoring of blood glucose by diabetic patients". Acta Endocrinol. Suppl., vol. 238, pp. 145-155, 1980.

* cited by examiner

*Primary Examiner*—Eric F. Winakur
(74) *Attorney, Agent, or Firm*—Nath & Associates; Viviana Amzel; Lee C. Heiman

(57) ABSTRACT

A method is provided for determining the level of an analyte in the blood of an individual by measuring the level of the analyte in an interstitial fluid or in any other non blood fluid which does not contain red blood cells and adjusting the measurement value by the concentration of at least one reference analyte.

10 Claims, No Drawings

METHOD AND KIT FOR THE TRANSDERMAL DETERMINATION OF ANALYTE CONCENTRATION IN BLOOD

FIELD OF THE INVENTION

This invention concerns a method for determination of the concentration of various analytes in the blood of an individual and kits for carrying out the method of the invention.

PRIOR ART

The following is a list of prior art publications referred to in the present specification.
Aronowitz, J. L. and Mitchen, J. R., PCT Application Publication No. WO 99/13336
Ben-Aryeh, H., et aL, *J. Diabet. Complications*, 2:96–99 ((1988).
Brown, L. R. and Edelman, E., PCT Application Publication No. WO 99/67645
Doneen, B. A., et al, PCT Application Publication No. WO 99/22639.
Forbat, L. N., et al., *J.R. Soc. Med.*, 74:725–728 (1981).
Guy, R. and Rao, G., U.S. Pat. No. 5,362,307.
Hertig, B. A. et al "Time course of sweating in warm baths" in: Montagna W. et al (eds.) Advances in biology of skin, Vol III Eccrine Sweat Gland and Eccrine Sweating, pp: 213–225, Pergamon Press, 1962
Kuno, Y., Human Perspiration, Charles C. Thomas, Publisher, USA, 1956
Patrick, A. W., et al., *Diabet. Med.*, 11:62–65 (1994).
Rothman, S., Physiology and Biochemistry of the Skin, Chapter 19: Carbohydrates, The University of Chicago Press, 1954
Sönsken P H, *Acta Endocrinol. Suppl.* (Copenhagen) 238: 145–155 (1980).

The acknowledgement herein of the above art should not be construed as an indication that this art is in any way relevant to the patentability of the invention as defined in the appended claims.

BACKGROUND OF THE INVENTION

Diabetes type I (insulin dependent) patients are required to frequently test their blood glucose levels. In 1993, a ten year long diabetes care and complications trial (DCCT) showed that the preferred mode of treatment of insulin dependent diabetes (Type 1) was by frequent small-dose administrations of insulin to such patients and determining the glucose level after each such administration. To follow such a treatment, a diabetic patient is required to puncture his skin and obtain a drop of blood for the glucose test at least three times a day. Such a frequent and repetitive puncturing is painful and often results in infection and formation of hard scar tissue and as a result, many diabetic patients neglect to sufficiently test their glucose level.

In an attempt to minimize the harm and pain caused by skin puncturing to obtain a blood specimen, alternative methods have been developed. Those methods generally belong to one of the following approaches:

(a) Non-invasive techniques, which are based on the analysis of transmission, scattering or reflectance spectra of various radiations, such as infra-red, photoacoustic and di-electric radiation, which permeate through the skin or other tissues.

(b) Minimally invasive techniques, which are based on drawing out minute specimens of blood or other fluids (sometimes referred to as "interstitial fluid"), in a manner which causes minimal pain or damage, or none at all.

Guy and Rao (U.S. Pat. No. 5,362,307) have shown a method for determining the concentration of an inorganic or organic substance in an individual by obtaining an interstitial fluid sample from the individual by a process called iontophoresis. In accordance with this method, an electric field is employed, causing the transdermal migration of ions, which carry with them non-charged molecules, such as glucose. This method was recently developed into the GlucoWatch™ product, by Cygnus, Inc., Redwood City, Calif., USA.

Methods for the extraction of glucose and other analytes from the skin, employing chemicals, called "enhancers" or "permeators" (herenafter "permeation enhancers") were recently described. Aronowitz and Mitchen (PCT WO99/1336) employ a gel, containing propylene glycol. The extracted fluid enters a gel and the concentration of glucose or any other analyte, is determined by a calorimetric reaction. Brown and Edelman (WO99/67645) also use a gel, containing pyrrolidone compounds and optionally other enhancers, to extract the analytes of interest from the skin. Both approaches require placement of gel on the skin for a defined length of time, which extends to more than 10 minutes, in order to ensure sufficient quantity of analyte, which will reflect the concentration of the same analyte in the blood.

Another minimally invasive method for obtaining a body fluid is that of SpecRx, Inc. Norcross, Ga., USA. A minute and shallow round hole is created in the skin, extending just below the stratum corneum and a sample of interstitial fluid is collected through this hole. That fluid is then tested for its glucose content by one of the methods known in the art.

In such minimally invasive methods the concentration of the tested substance in the obtained interstitial fluid sample may not always correctly indicate the level of the same substance in the blood of the tested individual at the time in which the sample was obtained or shortly thereafter. This is mostly due to the fact that the concentration of the tested substance varies in different locations in the body and at different hours of the day. Moreover, although such minimally invasive methods attempt to reduce the pain and damage normally associated with blood sampling, they still often result in discomfort to the tested individual, and involve skin irritation and damage.

Attempts to detect the correct glucose level in the blood by determining the level of glucose in fluids of body samples other than blood such as saliva, urine or tears were found to be non suitable since the concentration of the glucose in such fluids was shown to be variable and, more often than not, did not directly reflect the concentration of the glucose in the blood at the relevant point in time (Sönsken, Patrick et al, Forbat et al, Ben-Aryeh et al, Doneen et al.).

SUMMARY OF THE INVENTION

In accordance with the present invention it has been unexpectedly demonstrated that glucose in the interstitial fluid is spontaneously extracted from a non-wounded skin when the skin is contacted with water, containing no skin permeation enhancers. It was shown that the concentration of glucose in the blood can be inferred from the concentration of glucose in the skin water extract by the determination of a reference analyte in the extract and calculating a ratio. In accordance with the invention various electrolytes (preferably calcium ions) were found to be suitable reference analytes. The skin extraction with water was rapid: measurable levels of glucose and electrolytes were present in the specimen as early as 30 seconds following the initial contact between skin and water. The phenomenon of glucose extraction from the skin into water does not seem to be related to sweating, since sweat is not secreted when the skin is submerged in water (Hertig et al. 1962, Kuno 1956). Moreover, the invention demonstrated the ability to follow the changing concentration of glucose in blood by following glucose ingestion in skin extracts. This finding is unexpected in view of the observation that skin glucose level does not respond quickly to blood glucose variation, especially when the blood concentration falls following a hyperglycemic period (Rothman 1954).

By its first aspect, the present invention thus provides a method for determining the level of an analyte in the blood of an individual by measuring the level of said analyte in an interstitial fluid or in any other non blood fluid which does not contain red blood cells and adjusting the measurement value by the concentration of at least one reference analyte.

By a preferred embodiment the tested analyte is glucose.

By an additional preferred embodiment said reference analyte is calcium ions.

The invention further provides a method for determining the level of an analyte in the blood of an individual comprising:

(i) contacting the skin of said individual with water to obtain a water specimen;
(ii) determining the level of said analyte in said water specimen;
(iii) determining the level of one or more reference analytes in the water specimen;
(iv) calculating the level of said analyte in the blood of the tested individual based on the measurements in (ii) and (iii).

In accordance with one embodiment of the invention, the water contacted with the skin contains no skin permeation enhancers (such as for example, N-methyl pyrrole) used for extracting the analyte from the skin.

The term "level" as it is to be understood in the context of the present invention relates either to a quantity or to the concentration of the tested analyte.

The tested analyte may be any substance or component found in the blood for example, sugars, proteins, organic compounds etc., which is present in detectable amounts in the non-blood fluid or sample.

The term "interstitial fluid" is the fluid that is located outside blood vessels or extracted from tissues and does not contain blood and blood cells, but may contain non-cellular blood components.

The term "contacting" typically refers to immersion of an individual's skin in water or touching of an individual's skin with a water volume. The contact of the skin with the water does not involve disruption or induction of discontinuity of the skin and leaves the skin non-wounded.

The skin may be contacted with the water directly and without assistance of any special means. In such a case, typically several drops of water are placed on a solid surface (e.g. plastic or glass), the skin area is washed (e.g. with detergents and water), rinsed in water and air dried and then placed in the drop of water for a short period of time (typically about 30 sec.). The water is then collected from the surface and subjected to the assay. However, preferably, in accordance with the invention the skin is contacted with the water through a fine mesh (such as Polymon PES 180/31, obtainable from Sefar, Switzerland) which assists in spreading the water over the skin and thus promotes efficient extraction of the analytes from the skin.

The term "water" encompasses any kind of water including tap water, distilled water, water to which electrolytes were added, etc. In accordance with the invention the water does not contain any permeation enhancers.

The term "specimen" relates to a water sample obtained by said contact of the skin with water immersion of an individual's skin in water or touching an individual's skin to a water volume.

In accordance with the invention, any skin area may be contacted with the water, however it is preferable that the the skin area is a hairless skin area that does not have fat glands and, therefore, it is more accessible for testing. Examples of such areas are skin on the palms of hands and fingertips. Contacting a larger area of skin will yield higher levels of analytes.

The level of the tested analyte in the obtained sample is determined using any of the methods known in the art which are suitable for determining the level of the specific analyte to be tested. By a preferred embodiment of the invention the tested analyte is glucose. The level of the glucose in the body sample may be determined using any of the known highly sensitive glucose determination methods based on fluorescence, chemiluminescence, or bioluminescence. Examples of such methods are continuous monitoring of reactions that produce NADH and NADPH using immobilized luciferase and oxido reductases from *Beneckea harveyi* (Haggerty, C. et al., *Anal. Biochem.*, 88:162–173, 1978 or Jablonski, E., et al., *Clin. Chem.*, 25:1622–1627, 1979). In addition, any of the cholorimetric or electrochemical methods known in the art which utilize glucose oxidase or glucose dehydrogenase or hexokinase may also be used for determining the level of the glucose in the sample (see for example Sigma Cat #: 315, 115-A, 510-A).

The reference analyte can be any analyte, which is normally present in the body (e.g. in the blood). In accordance with the invention one or more reference analytes may be used. The analyte can be from the group of proteins, carbohydrates, lipids, proteins or electrolytes. Electrolytes are preferable to other components due to their stability and ease of measurement. Although sodium is the most abundant electrolyte in the body, calcium ions may be preferable as a reference due to (a) the tight physiological of the calcium level; (b) the abundance of sodium in nature may interfere with determination of low levels of analyte in very dilute specimens.

Calcium levels can be easily determined by a variety of methods known in the art. In addition, ready reagent kits for calcium determination are available from many manufacturers of in vitro diagnostics, such as Sigma Chemicals, St. Louis, Mo., USA and Merck, Darmstadt, Germany Calculation of the concentration of the tested analyte may be based on the ratio of the concentration of the analyte, which was measured in the obtained sample to the concentration of the reference component measured in the same. For example, wherein the tested analyte is glucose and the reference component is calcium ion, the glucose concentration in the blood of the tested individual is calculated from the ratio of the glucose to calcium ion.

The measurement of the glucose in the water extract is corrected by the measurement of the electrolyte level in the specimen. In some cases, calculating the simple ratios of the analyte to the reference analyte may provide a good precision in calculating the level of the tested analyte. In other cases calculation of the simple ratio may result in a comparatively low precision. In such a case, logarithmic transformation of the analyte measurement (using the formula: 1000× log 10 [analyte]/[reference analyte]) may yield a better precision and may be used in accordance with the invention.

By an additional aspect of the invention, a kit is provided for determining the level of an analyte in the blood of a tested individual comprising:
 (i) a collecting member obtaining a water specimen from skin of said individual;
 (ii) a measurer measuring the level of the tested analyte in the obtained sample;
 (iii) a measurer measuring the level of a reference analyte in the sample;

said collecting member may be a container in which the water is collected directly from the individual's skin or a solid surface (e.g. plastic or glass) from which the water is collected into a container.

Optionally, the kit may also comprise a calculator calculating the level of said tested analyte in the blood of the tested individual on the basis of the measurements obtained in (ii) and (iii) above.

The above kit may further comprise a test strip incorporating the reagents or structures necessary to carry out the measurement of the tested analyte as well as the reference analyte. In such a case, an instrument into which the test strip can be inserted or to which the test strip may be connected, is also included in the kit. Such an instrument, which may be portable, is capable of detecting and analyzing the signal emitted by the test strips and optionally may translate them directly into prevalent units.

EXAMPLES

The invention will now be demonstrated by way of the following non-limiting examples.

Example 1

Reagents and Method for Luminometric Determination of Glucose

Preparation of Luminol Concentrate

The following mixture was prepared in a disposable polystyrene test tube:
 100 μL of Sodium Luminol stock solution of 40 mg/mL $H_2O$
 14.6 μL of p-iodophenol stock solution of 100 mg/mL DMSO
 1886 μL $H_2O$
The mixture was stored at 4° C. until use.

Preparation of Luminometric Enzyme Mix

The following mixture was prepared in a disposable polypropylene test tube:

0.6 mL Glucose Oxidase stock of 4400 U/mL $H_2O$
 1.2 mL Horseradish Peroxidase stock of 1100 U/mL $H_2O$
 0.6 mL 0.5M Tris-HCl, pH 8.5
 2.6 mL isotonic Sodium Fluoride solution (1.75% w/v in $H_2O$)
 625 μL 20% Bovine Serum Albumin (Cohn's Fraction V) in isotonic
 Sodium Fluoride solution
 625 μL Luminol concentrate For test: 5 μL sample was placed in the bottom of a Microfuge tube. The tube was inserted into the counting chamber of a Labsystems Luminoskan TL Plus. 45 μL of the luminometric mix was added, the lid of the counting chamber was lowered into closed position and counting proceeded for 1 second.

Example 2

Comparison Between Calcium and Magnesium as Reference Analytes in the Determination of Blood Glucose in Skin Extract 1 $cm^2$ pieces of polyester mesh (Polymon PES 180/31, Sefar, Rüschlikon, Switzerland) were washed extensively in distilled water and dried at 70° C. Fifty μL aliquots of distilled water were placed on the skin at different locations of the arm. A 1 $cm^2$ piece of polyester mesh was placed over each drop of water and facilitated its spreading. Following 30 seconds, the piece of mesh was centrifuged briefly at 10,000×g to extract the fluid. The glucose in the fluid was tested by luminometry, as described in Example 1. Magnesium was tested by the Mg-Kit and calcium ion was tested with the Ca-Kit, both kits obtained from bioMérieux, Marcy l'Etoile, France. The skin specimen collection was conducted under fasting conditions, so as to ensure constant blood glucose concentration. Before calcium or magnesium determination, the pH of the specimen was determined employing pH test strips of the fixed color type (Sigma Chemical Co., St Louis, Mo., USA). In all cases the pH was not more than 6.0, thus ensuring that the cations are not complexed.

The results of the measurements are presented in Table 1 below utilizing the following units:
 glucose—counts per second
 calcium and magnesium—OD×1000

The glucose measurement is corrected by the electrolyte level, which should reflect the volume of blood or interstitial fluid. By calculating the simple ratios of glucose to electrolyte the precision was not acceptable (57–73%). However, a logarithmic transformation of the glucose measurement (using the formula: 1000×$Log_{10}$[glucose]/[electrolyte]) yielded a good 13% precision, when the Calcium level is employed for correction. Employing the magnesium concentration for correction did not yield an acceptable precision.

TABLE 1

| Specimen ID | Raw Data | | | net | | | Ratios | | Log glu ratios | |
|---|---|---|---|---|---|---|---|---|---|---|
| | Glu | Mg | Ca | Glu | Mg | Ca | Mg | Ca | Mg | Ca |
| Reaction blank | 788 | 835 | 292 | −2985 | 0 | 0 | | | | |
| 1 | 23701 | 871 | 328 | 19928 | 36 | 36 | 554 | 554 | 119 | 119 |
| 2 | 55599 | 874 | 342 | 51826 | 59 | 50 | 886 | 1037 | 81 | 94 |
| 3 | 8130 | 854 | 320 | 4357 | 19 | 28 | 229 | 156 | 192 | 130 |

TABLE 1-continued

| Specimen | Raw Data | | | net | | | Ratios | | Log glu ratios | |
|---|---|---|---|---|---|---|---|---|---|---|
| ID | Glu | Mg | Ca | Glu | Mg | Ca | Mg | Ca | Mg | Ca |
| 4 | 15045 | 851 | 325 | 11272 | 32 | 33 | 352 | 342 | 127 | 123 |
| Mesh Blank | 3773 | 837 | 294 | 0 | 2 | 2 | 0 | 0 | | |
| Average: | | | | | | | 505 | 522 | 130 | 117 |
| Precision (%): | | | | | | | 57 | 73 | 36 | 13 |
| Glu 0.1 mg/dL | 68503 | | | 67715 | | | | | | |
| Ca 100 mg/L | | | 696 | | | 404 | | | | |
| Mg 25 mg/L | | 1165 | | | 330 | | | | | |

Example 3

Effect of mesh on analyte levels in skin water extract The significance of mesh in extracting glucose and calcium from the skin was subject to the following test.

For fingertip sampling, one hundred $\mu$L drops of distilled water were placed on a flat piece of sterile polystyrene (the lid of a 24-well tissue culture dish, Corning Glass Works, Corning, N.J., USA). In case of "No-mesh" sampling, the fingertip was washed first with detergent and water, followed by rinsing in about 50 mL of distilled water and air-dried. The washed fingertip was placed in the drop of distilled water for 30 seconds. The remaining water on the polystyrene surface was collected by a micro-pipetter and stored in a Microfuge tube. In case of mesh sampling, a 1 cm$^2$ piece of polyester mesh was placed over the drop of water (on the polystyrene surface) and the washed fingertip was placed on the mesh for 30 seconds. Following 30 seconds, the piece of mesh was centrifuged briefly at 10,000×g to extract the fluid.

For hand sampling, the palm of the hand was washed first with detergent and water, followed by rinsing in about 50 mL of distilled water and air-dried. A one-hundred $\mu$L aliquot of distilled water was placed on the inner skin of the palm of the hand. In case of "No-mesh" sampling, the water was collected by a micro-pipetter and stored in a Microfuge tube. In case of mesh sampling, a 1 cm$^2$ piece of polyester mesh was placed over the drop of water and facilitated its spreading. Following 30 seconds, the piece of mesh was centrifuged briefly at 10,000×g to extract the fluid The glucose in the specimens was tested by luminometry, as described in Example 1. Calcium ion was tested with the Ca-Kit, (bioMérieux, Marcy l'Etoile, France).

A comparison of the amounts of glucose and calcium obtained from fingertip and palm skin extracts with and without mesh is shown in Table 2 below.

TABLE 2

| | No mesh | | With mesh | |
|---|---|---|---|---|
| Specimen | Glucose cps | Ca++ (OD × 100) | Glucose cps | Ca++ (OD × 100) |
| Finger | 18246 | 28 | 114654 | 83 |
| Hand | 107697 | 130 | 222287 | 269 |

Standard values: 0.1 mg/dL glucose=170807 cps;
100 mg/L Ca$^{++}$=379 (OD×100)

As seen in Table 2, employing mesh increases the level of analytes in skin extracts.

Example 4

Comparison Between Blood and Skin Glucose Testing in a Glucose Loading Experiment Glucose loading experiment was conducted as follows:

Following an overnight fast, the capillary blood glucose level of the test subject was determined employing the OneTouch® system (LifeScan, Inc., Milpitas, Calif., USA). Immediately thereafter the skin glucose and calcium ion levels were determined, as described in Example 1, except that a 100 $\mu$L aliquot of water was employed.

Upon completion of the skin specimen processing, 50 gr glucose (generic, food grade) were suspended in club soda water with fresh lemon juice and ingested immediately. Forty five minutes thereafter, both capillary blood glucose and skin glucose+calcium ion measurements were taken. A third measurement of the blood and skin analytes was conducted about an hour or more later, when it could be shown that the blood glucose level was declining.

The glucose results are presented in arbitrary units derived from dividing the luminometric glucose measurement in cps (counts per second) by the value obtained by multiplying the OD (optical density) of the calcium ion test mix. Skin measurements were taken in triplicate. Standard glucose (0.1 mg/dL) and Calcium (100 mg/L) solutions were tested with each skin measurement. Glucose results were adjusted to a standard measurement of 200,000 cps and calcium results were adjusted to OD×100 of 400.

The results of two separate experiments are shown in Tables 3 and 4 below.

Table 3 summarizes measurement conducted on the hairless skin area of the forearm:

TABLE 3

| Time | Blood mg/dL | Ratio Log Glucose/OD Ca | Notes |
|---|---|---|---|
| 8:02 | 87 | 61 ± 10 | Fasting |
| 9:58 | 130 | 130 ± 10 | 45 min past challenge |
| 10:40 | 111 | 101 ± 17 | |

Table 4 summarizes measurement conducted on the palm of the hand:

TABLE 4

| Time | Blood mg/dL | Ratio Log Glucose/OD Ca | Notes |
|---|---|---|---|
| 8:01 | 90 | 84 ± 20 | Fasting |
| 8:55 | 127 | 172 ± 5 | 45 min past challenge |
| 10:50 | 99 | 155 ± 22 | |

In both cases it is clear that the determination of glucose in a skin extract follows the kinetics of the capillary blood glucose.

The invention claimed is:

1. A method for determining the level of an analyte in the blood of an individual, comprising the steps of:
   (i) measuring the level of said analyte in an interstitial fluid or in any other non blood fluid obtained non-invasively from the skin of a tested individual, wherein said interstitial fluid or any other non blood fluid does not contain red blood cells, and
   (ii) adjusting the measurement value by the concentration of at least one reference analyte measured in said interstitial fluid or in said any other non blood fluid of step (i), thereby determining the level of said analyte.

2. A method according to claim 1, wherein said sample is obtained without the use of skin permeation enhancers.

3. A method according to claim 1, wherein said analyte is glucose.

4. A method according to claim 1, wherein said at least one reference analyte is an electrolyte.

5. A method according to claim 4, wherein said electrolyte is a calcium ion.

6. A method for determining the level of an analyte in the blood of an individual comprising:
   (i) contacting the skin of said individual with water to obtain a water specimen;
   (ii) determining the level of said analyte in the water specimen of step (i);
   (iii) determining the level of one or more reference analytes in the water specimen of step (i); and
   (iv) calculating the level of said analyte in the blood of the tested individual based on the measurement in (ii) and (iii).

7. A method according to claim 6, wherein said water contacted with the skin of said individual does not contain skin permeation enhancers.

8. A method according to claim 6, wherein said analyte is glucose.

9. A method according to claim 6, wherein said at least one reference analyte is an electrolyte.

10. A method according to claim 9, wherein said electrolyte is a calcium ion.

* * * * *